United States Patent
Davis

(10) Patent No.: US 6,524,102 B2
(45) Date of Patent: Feb. 25, 2003

(54) METHOD AND APPARATUS FOR APPLYING THERMOPLASTIC BORDER MOLDING TO DENTURE IMPRESSION TRAYS

(76) Inventor: Kerry N Davis, 3601 Twinbreeze Way, Las Vegas, NV (US) 89129

( * ) Notice: Subject to any disclaimer, the term of this patent is extended or adjusted under 35 U.S.C. 154(b) by 14 days.

(21) Appl. No.: 09/733,816

(22) Filed: Dec. 8, 2000

(65) Prior Publication Data

US 2002/0072030 A1 Jun. 13, 2002

(51) Int. Cl.$^7$ ............................................. A61C 3/00
(52) U.S. Cl. ..................... 433/32; 433/214; 222/146.5; 401/2
(58) Field of Search ........................... 433/32, 214, 37, 433/48; 222/146.5; 219/221, 227, 229; 401/1–3

(56) References Cited

U.S. PATENT DOCUMENTS

| | | |
|---|---|---|
| 3,522,654 A | 8/1970 | Schoelz |
| 3,614,389 A | 10/1971 | Malisza |
| 3,665,158 A | 5/1972 | Froedge |
| 3,744,921 A | 7/1973 | Weller et al. |
| 4,265,618 A | 5/1981 | Herskovitz |
| 4,546,235 A | 10/1985 | Kolter |
| 4,773,566 A | 9/1988 | Hoagland |
| 4,816,642 A | 3/1989 | Dennison |
| 5,026,187 A | 6/1991 | Belanger et al. |
| 5,462,206 A | 10/1995 | Kwasie |
| 6,105,824 A | 8/2000 | Singleton |
| 6,312,254 B1 * | 11/2001 | Friedman ................ 433/32 |

OTHER PUBLICATIONS

Predictable impression procedures for complete dentures, Felton DA et al., Dent Clin North Am 1996 Jan; 40(1):39–51.

Variability in the shape of maxillary vestibular impressions recorded with modeling plastic and a polyether impression material, Tan HK et al., Int J Prosthodont 1996 May–Jun.; 9(3):282–9.

Complete denture impressioning technique, Kois JC et al., Compend Contin Educ Dent 1997 Jul.; 18(7):699–704, 706–8; quiz 710.

A technique for border molding edenttulous impressions using vinyl polysiloxane material, Chaffrr NR et al., J Prosthodont 1999 Jun.; 8(2):129–34.

Making accurate final impressions for the fabrication of complete dentures. 1: Maxillary impressions, Clancy JM et al., Iowa Dent J 1990 Oct.; 76(4):1–3.

Predictable impression procedures for complete dentures, Felton DA er al., Dent Clin North Am 1996 Jan.; 40(1):39–51.

Variability in the shape of maxillary vestibular impressions recorded with modeling plastic and a polyether impression material, Tan HK et al., Int J Prostodont 1996 May–Jun.;9(3):282–9.

Jefferson F. Hardin, Editor–in–Chief, Clark's Clinical Dentistry, vol. 5, Revised Edition–1989, J.B. Lippincott Company, Chpt. 11, pp. 18–21.

* cited by examiner

*Primary Examiner*—Cary E. O'Connor
(74) *Attorney, Agent, or Firm*—Quirk & Tratos

(57) ABSTRACT

A method and apparatus for providing clearances in the edges of a denture to accommodate the adjacent anatomical landmarks utilizes a molding compound dispenser in which a sufficient quantity of molding compound to cover the edges of an impression tray is maintained in a limited temperature range above melting temperature. The dispenser may be provided with heat exchange surfaces that can be selectively covered by the practitioner's hand to control the amount of heat loss to the surroundings. Manual pressure may be used to deposit the compound onto the edges.

13 Claims, 4 Drawing Sheets

METHOD AND APPARATUS FOR APPLYING THERMOPLASTIC BORDER MOLDING TO DENTURE IMPRESSION TRAYS

BACKGROUND OF THE INVENTION

1. Field of the Invention

The present invention relates to denture fabrication processes, and more particularly to a process and apparatus for applying thermoplastic impression compound molding onto custom denture impression trays.

2. Description of the Prior Art

The process of fabricating dentures entails a variety of steps each necessary to properly conform the denture interface to the unique muscular and skeletal architecture of the patient. It is a time consuming, elaborate process. In accordance with the currently prevailing practice a customized denture impression tray is first fabricated, generally conforming with the maxillary or mandibular structure of the patient, with the peripheral edges of the tray shortened or reduced to accommodate molding compound impressions of the adjacent anatomical landmarks. These molding compound impressions are made in a border molding bead applied onto the peripheral edges of the tray which is repositioned into the patient while the compound is still soft. The patient is then asked to perform various movements of the facial musculature while the border molding compound is setting to provide in the impression appropriate clearances within the buccal, labial and/or lingual folds. When these borders are thus defined the rest of the tray is filled with impression material to provide a full impression of the denture interface.

In this process the desired border molding compound is one of several thermoplastic compounds having a setting temperature just somewhat higher than the patient's body temperature. The minimal difference between a tolerable temperature, i.e., temperature at which tissue is injured, and the temperature within the patient's oral cavity leaves little working range. Within this marginal temperature range the molding compound must be applied as a ribbon or bead along the denture impression tray borders, and thereafter fitted to the patient while still soft. Of course, the bead would frequently set up along the ribbon length and the incidence of improper impression because of already hardened molding compound was both an unwanted and an anticipated event. The practitioner was therefore expected to re-heat the molding compound 'stick' and thereafter parts of the ribbon over an open flame, each time with some concern over excessive temperature levels that may injure the patient. The necessary experience and skill in this border molding process, together with the attention required, have substantially affected the cost of dentures and any simplification techniques would greatly enhance both the quality of the product and its cost. Amongst the simplifications the task directed at maintaining the border molding pliable while it is applied is the most cumbersome and therefore most likely to benefit from any improvement.

In the past various devices have been developed which in one way or another eject heated compounds in the course of dentistry. Examples of such devices are described in U.S. Pat. No. 3,522,654 to Schoelz and U.S. Pat. No. 3,614,389 to Malisza, both directed to electrically heated dental wax dispensers, and U.S. Pat. No. 4,265,618 to Herskovitz et al. describing endodontic syringes for dispensing thermoplastic material. While suitable for the purposes intended, each of the foregoing dispenses thermoplastic matter in quantities that are less than those that can pose substantial risk of burn injury, or that dispense molten substances onto those body elements that are generally resistive to heat.

Concurrent with these developments, those engaged in the adhesives art have also developed a variety of devices that in one manner or another melt matter for use as a glue or adhesive. Examples of such devices include those taught in U.S. Pat. No. 5,026,187 to Belanger et al., U.S. Pat. No. 5,462,206 to Kwasic, U.S. Pat. No. 4,773,566 to Hougland, U.S. Pat. No. 3,744,921 to Weller et al. and others. Again, while wholly suitable for the purposes intended, each of the foregoing dispensers seeks to maximize the best transfer to the thermoplastic material, and considerations of tissue injury are attended primarily by protective structure and shielding.

Also devised in the part are molten adhesive dispensers which include automatic cut-outs, like those taught in U.S. Pat. No. 4,546,235 to Költer and U.S. Pat. No. 6,105,824 to Singleton, and those provided with temperature controllers like those shown in U.S. Pat. No. 3,665,158 to Froedge and U.S. Pat. No. 4,816,642 to Dennison. Each of these, while well suited for its purpose, lacks the requisite control and heat exchange configuration that is required for dispensing matter within the limited temperature range bounded by normal body temperature and the temperatures associated with tissue injury.

Those in the art will appreciate that normal heat transfer exchanges between body temperature to the temperatures of the ambient environment will occur with some expedience, particularly if the surface-to-volume ratio of the heated mass is high. These heat transfer conditions, and the maximum temperature limits of any matter that will contact human tissue, require high volumes of stored molten compound for quick, large quantity dispensing of the border bead. A method and structure adapted to these narrow constraints is extensively sought, and it is one such process and structure that is disclosed herein.

SUMMARY OF THE INVENTION

Accordingly, it is the general purpose and object of the present invention to provide a dispenser useful in heating and dispensing thermoplastic molding compound limited in temperature range.

Other objects of the invention are to provide a process for dispensing thermoplastic molding compound in large quantities.

Further objects of the invention are to provide a dispensing structure useful in heating large quantities of thermoplastic molding compound within a limited temperature range.

Yet additional objects of the invention are to provide a method and structure for applying molten border molding material onto the edges of a custom denture impression tray that is limited in temperature range.

Briefly, these and other objects are accomplished within the present invention by providing a thermoplastic molding compound dispenser useful in heating hardened compound in cylindrical cartridges to a limited temperature above melting. More precisely, the dispenser is provided with a cylindrical heating chamber dimensioned for intimate surface contact with the exterior of the cartridge and surrounded by an electrical heating element. This heating chamber is aligned along the longitudinal axis of an elongate dispenser body terminating in a dispensing nozzle at its forward, and a cartridge receiving opening at the rearward end.

Preferably the heating element is positioned close to the forward end of the heating cavity, in series with a temperature control circuit provided with a sensor or thermocouple adjacent the nozzle. A set of radially extending hoops is attached to the body, rearward of the sensor, both to provide finger engagements in the course of dispensing and to serve as sufficiently large heat exchange surfaces for effective temperature control. Furthermore, a generally planar, lateral body extension rearward of the hoops provides the other manipulative structure while also accommodating heat exchange. The presence of such enlarged heat exchange surfaces allows for the closely regulated temperature control accommodating the narrow range of controlled heat ranges of the molding compound.

Preferably, the cavity volume heated by the electric element is sufficient to store the full quantity of the molding compound necessary for the complete border molding ribbon. Concurrently, the surface areas of the hoops and the handle structure selected for sufficient heat loss to overcome any gain due to the heat internally stored, limits any heat excursions beyond those set in the temperature control circuit. In this manner the surface-to-volume characteristics of the dispenser structure are useful in minimizing the potential of an unwanted temperature increase in the molten molding compound while also providing manipulative convenience.

The foregoing dispenser can then be utilized to lay a complete ribbon of molding compound in a single application, extending over the whole of the peripheral edge of the dental casting form which can thereafter be immediately positioned on the maxillary or mandibular surfaces of the patient. Once thus positioned, a well-known sequence of muscular manipulations can then be used to conform the border moldings to a set shape that accommodates the muscular surface distortions. In this manner the process of forming and constructing dentures is rendered convenient, allowing for a much more precise accommodation of the anatomical landmarks and much more comfortable denture.

DESCRIPTION OF THE PREFERRED EMBODIMENT

Figure 1:
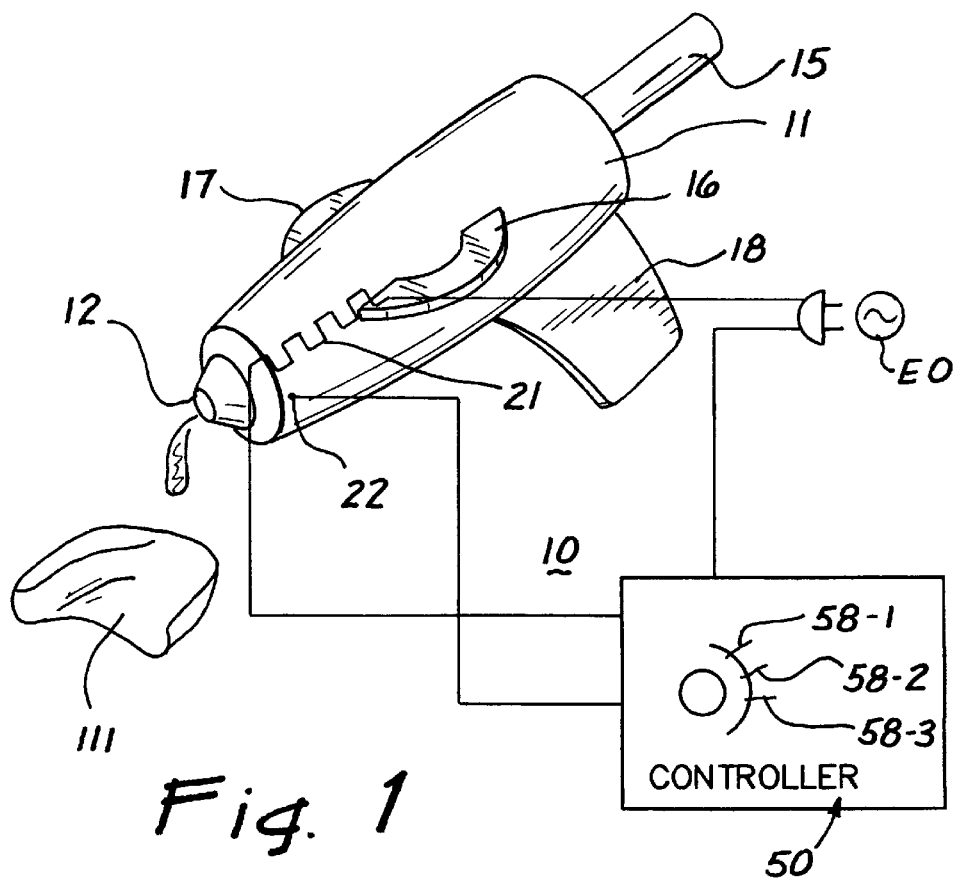
FIG. 1 is a perspective illustration of an inventive dispenser structure useful in applying thermoplastic border molding to the edges of a dental casting tray.

As shown if FIGS. 1–4 the inventive thermoplastic molding compound dispenser, generally designated by the numeral 10, includes an elongate, generally cylindrical body 11 provided with a nozzle insert 12 at the forward end communicating with a central cavity 14 extending through the body. Cavity 14 is circular in section conformed for a serial, intimate surface contact, receipt of cylindrical cartridges or 'sticks' 15 of hardened thermoplastic molding compound insertable into the cavity at the rearward end of body 11. Preferably each cartridge 15 comprises a thermoplastic material structure like that sold under the mark or style "Kerr Impression Compounds" by the KERR CORPORATION, 28200 Wick Road, Romulus, Mich. 48174-2600. In commercial practice these cylindrical cartridges or 'sticks' 15 are color-coded in accordance with their melting or softening temperature and are available in melting ranges of 122–124 degrees Fahrenheit, 128–130 degrees Fahrenheit and 132–133 degrees Fahrenheit. From these ranges the practitioner selects the appropriate temperature range based on the size of the task, the temperature of the surroundings and the sensitivity of the patient.

Each cartridge 15 is manually advanced, by thumb pressure, into cavity 14 until the first one bottoms out at the nozzle insert 12. In this placement the forward portion of the cartridge is aligned within the interior of a helical heating element 21 connected to an electrical outlet EO on one end and to a temperature controller 50 on the other end. Controller 50, in a manner described more precisely hereinbelow, then completes the other part of the circuit between the heating element 21 and the outlet EO.

More precisely, a temperature sensor 22 positioned within the body 11 in thermal communication with the cavity 14, proximate the nozzle 12, is useful to provide the actual temperature of the cartridge 15 within the cavity to be then compared against the temperature selected by the practitioner by way of a manual selection input through a potentiometer 51 on the controller 50. Of course, the temperature selected through the potentiometer 51 will be in accordance with one of the several temperature ranges of the cartridge 14 and a plurality of markings 58-1 through 58-3 is provided adjacent the potentiometer to facilitate the selection.

Figure 3:
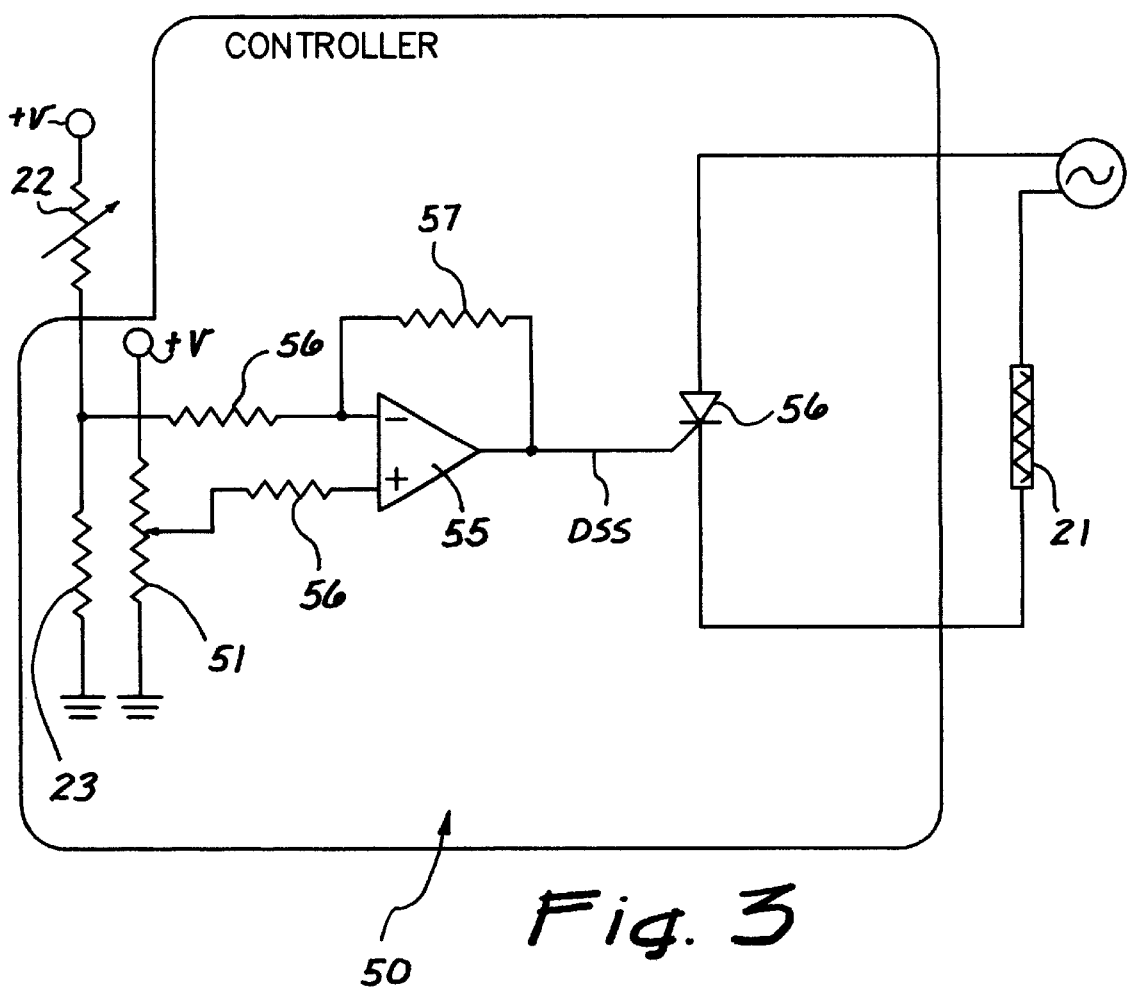
FIG. 3 is a circuit diagram of a temperature control circuit useful with the present invention.

In the implementation shown in FIG. 3 sensor 22 may be one of several types of temperature sensing devices, illustrated herein by way of a thermistor connected in a divider circuit across a resistor 23 to ground to form a divider circuit with its division point tied to the negative input of an operational amplifier 55. The other amplifier input, in turn, may receive the wiper signal of the potentiometer 51 through which the practitioner selects the temperature, with the amplifier 55 then summing the difference therebetween. This difference signal D55 is then useful to gate a silicon controlled rectifier SCR 56 in circuit between the filament 21 and the AC electrical outlet EO, controlling the power-on pulse duration across the heater. In this manner a substantially linear feedback control arrangement is devised controlling the compound temperature next to nozzle 12 to a temperature difference that is in an inverse ratio to the gain of the operational amplifier 55 selected by the ratio of a feedback resistor 57 and input resistors 56 between potentiometer 51 and thermistor 22.

To provide the requisite control authority and precision an opposite, heat loss, path is effected by way of planar structures extending from the body 11 that also serve as manipulative surfaces. More precisely, extending laterally from body 11, at a longitudinal location spaced rearwardly from the location of the heating element 21, are two opposed hoops 16 and 17 each dimensioned to receive the index and/or middle finger of the practitioner. Even further rearwardly is a planar projection 18 that is useful as a handle to be grasped by the palm when the fingers are inserted into the hoops. Once thus grasped the projecting portion of the last cartridge 15 can be pushed by the thumb to dispense the molten compound out of the nozzle 12.

Figure 4:
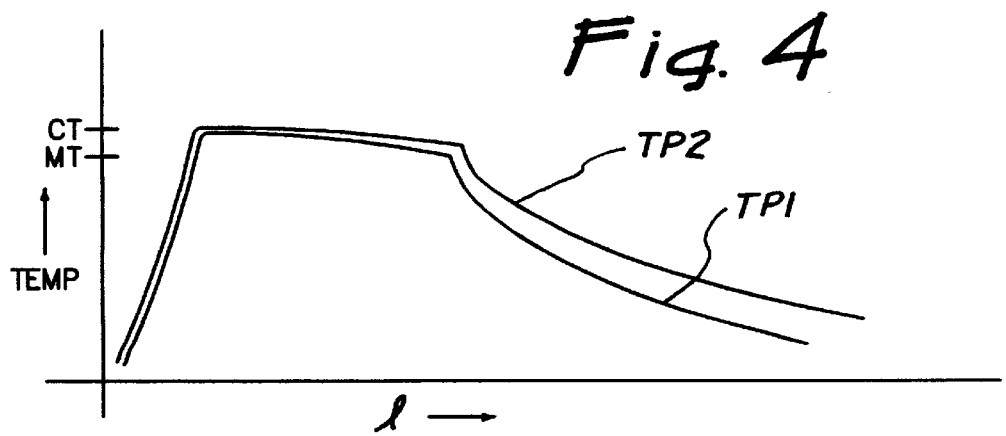
FIG. 4 is a graphical illustration of the temperature profiles based on surface-to-volume ratios along the longitudinal axis of the inventive dispenser.

In the foregoing implementation both the opposed hoops 16 and 17 and the surface of the handle 18 serve as effective heat exchange mechanisms. Those skilled in the art will appreciate that any heat exchange will follow the functions of the cube of the temperature difference for convective exchange and the fourth power of the difference for radiative exchange. An examplary temperature distribution profile TP1 is shown in FIG. 4 along the length of body 11, with the surfaces exposed to ambient exchange, against a profile TP2 corresponding to the temperature profile when the surfaces of hoops 16 and 17 and of handle 18 are within the palm of the practitioner. Thus the manipulative surfaces are cooperatively useful with the temperature control to modulate the heat loss and therefore the control loop error. By selecting a control temperature CT in potentiometer 51 that is close to the melting temperature MT of stick 14 this manual shielding of the exchange surfaces will be useful to an experienced practitioner in the process described below.

Figure 6:
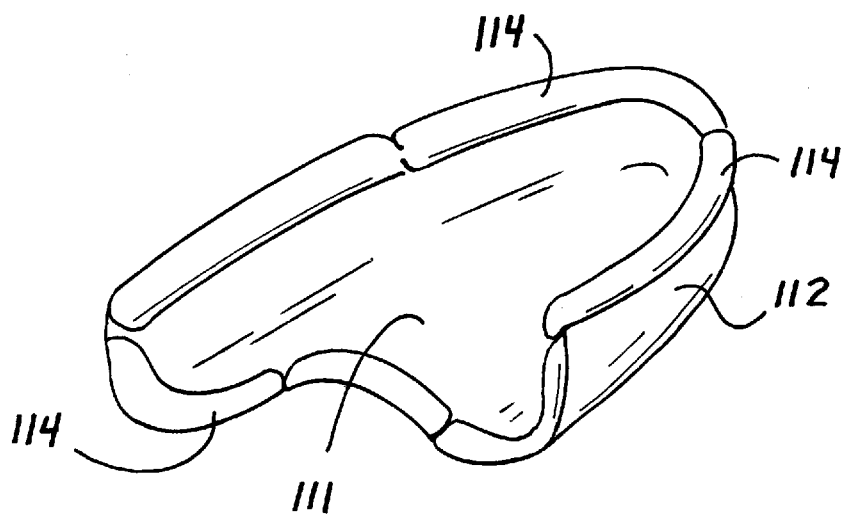
FIG. 6 is a perspective illustration of a custom denture impression tray having a peripheral bead of molding compound deposited thereon in accordance with the inventive process described herein.
Figure 5:
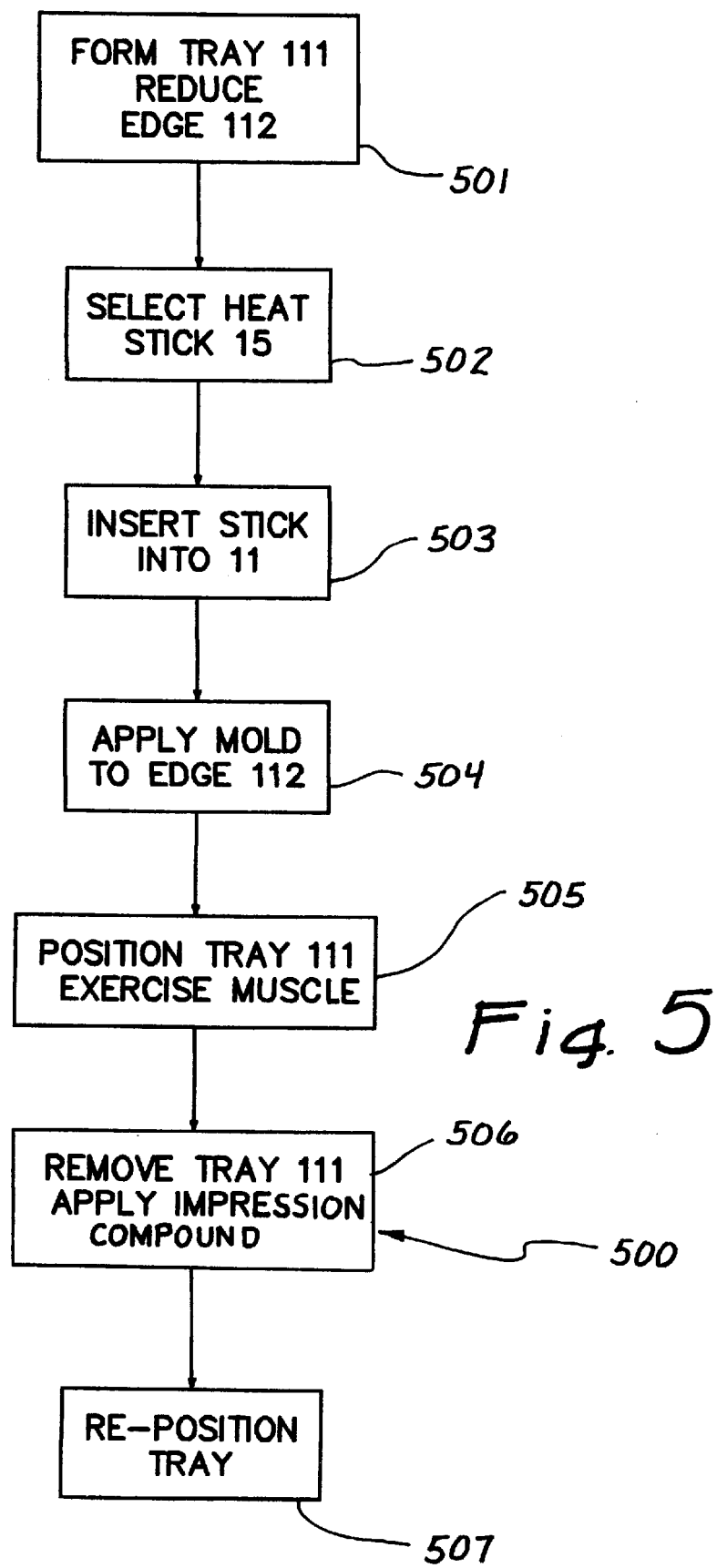
FIG. 5 is a flow chart of a sequence of steps in accordance with the inventive process disclosed herein.

As shown in FIGS. 5 and 6 the sequence of steps rendered possible by the dispenser 10, shown generally as process 500, commences with step 501 in which an impression tray 111 is formed to a general conformation with the maxillary or mandibular architecture of the patient. The peripheral edge 112 of the tray is reduced in height to provide clearance for the changing anatomy in the various folds within which the eventual denture is to be placed. Once the tray is thus formed sticks 15 are selected and the temperature corresponding thereto is set by way of the setting of potentiometer 51, both in step 502. In step 503 the selected sticks 15 are then serially inserted into cavity 14 with the last stick 15 exposed at the rearward end of body 11. The temperature controller 50 then heats the internally captured stick material to melting temperature and maintains it thereat as heat is given off the surfaces. In step 504 the practitioner grasps the dispenser 10 and by pressing on the exposed stick end applies a bead of molten compound 114 onto the peripheral edge 112 of the tray. In the course of this application the heat exchange rate is limited by the hand of the practitioner and the bead is therefore slightly warmer as result thereof. With the bead thus deposited the tray 111 is inserted in position adjacent the mandibular or maxillar anatomical structures in step 505 and the patient is then exercised through the necessary movements. In the course of these movements the anatomical landmarks of the patient deform the bead to provide the necessary clearances. Once the bead compound hardens the tray is removed in step 506 and impression compound is applied to the tray for the complete denture impression. Then in step 507 the tray is repositioned once more into the patient and a full impression is made.

Thus the inventive process facilitates a dental impression without the repeated instances of reheating that were the rule in the past. As result accuracy of the denture interface is improved while the process is also simplified. Great economies in the cost of a denture are therefore realized in a process that has also been rendered more accurate.

Figure 7:
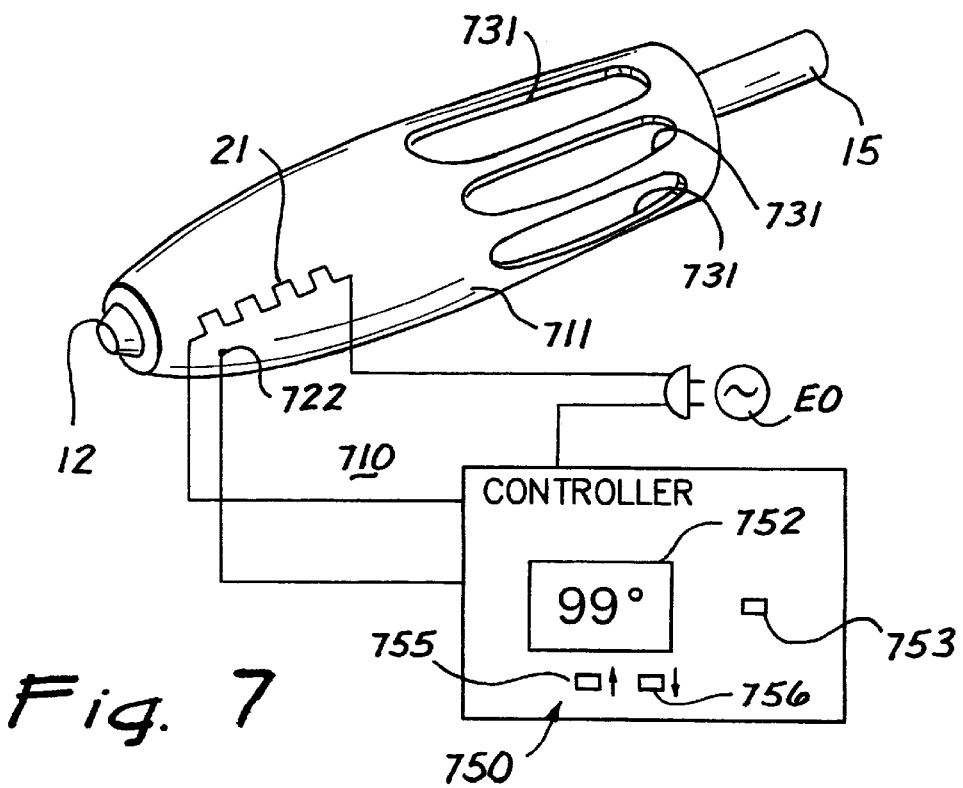
FIG. 7 is a further perspective illustration of an alternative implementation of a dispenser structure in accordance with the present invention.
Figure 2:
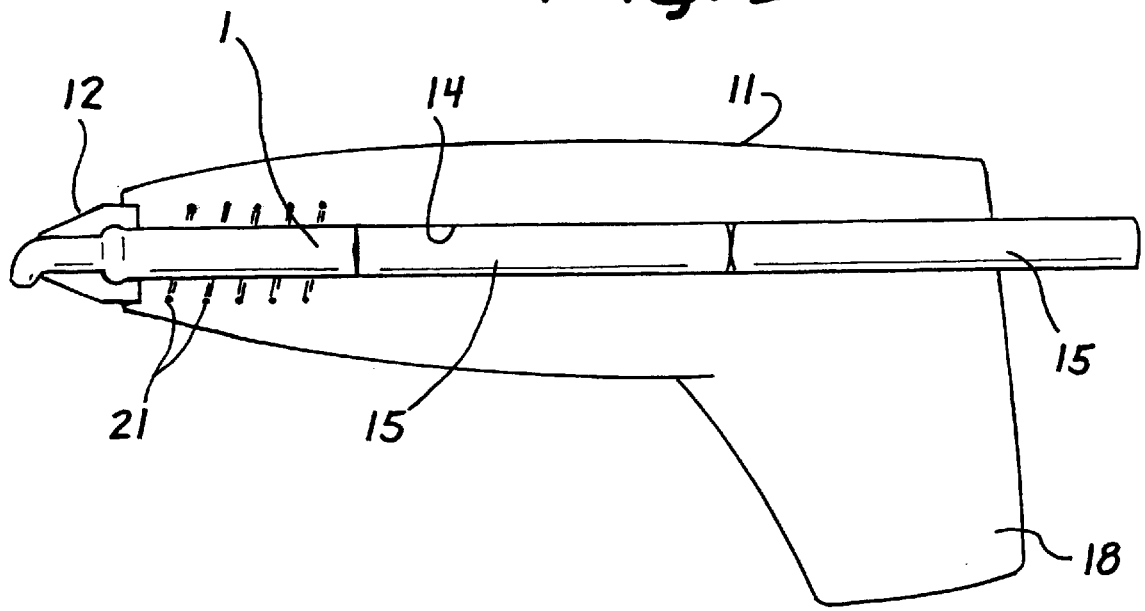
FIG. 2 is a side view in partial section, of the inventive dispenser illustrated in FIG. 1.

While the foregoing is achieved by way of the control circuit set out in FIGS. 1–4, other dispenser implementations are equally useful. Thus as shown in FIG. 7 a molding compound dispensing system generally designated by the numeral 710 once again includes an elongate body dispenser 711 connected to across a controller assembly 750 again to the electrical outlet EO. Like numbered parts functioning in the manner previously described, the dispenser body 711 is provided with the central cavity 14 conformed to receive in a sequence cartridges 15 advanced towards a forward nozzle 12 by thumb pressure. At the forward end cavity 14 is once more surrounded by a helical heating filament 21 in circuit with the controller 750 which may be one of the several commercially available controllers exemplified by the microprocessor implemented controller sold under the model no., mark or style CN491A by Omega Engineering, Inc., One Omega Drive, Stamford, Conn. 06907-0047. Controllers of this type are generally adapted to accommodate a wide variety of input devices and are also conformed to provide linear output to the filament 21 either by current level, voltage level or pulse width. In the implementation herein the controller 750 receives the temperature information by way of a thermocouple 722 mounted, as hereinbefore set out, adjacent nozzle 12.

Controller 750, in accordance with the commercial implementation thereof, is provided with a numerical temperature display 752 positioned adjacent a selector switch 753 through which the display mode is selected between a temperature readout of the temperature sensed by the thermocouple 722 or the temperature control input effected manually by an up switch 755 and a down switch 756. In a manner known in the art controller 750 modulates either the voltage or the current applied to the heating filament 21.

Those in the art will appreciate that other control techniques can be utilized in the course of practicing the present invention. For example, an on-off technique can be effected by providing sufficient control authority (heat gain vs. heat loss), which are respectively effected by the thermal capacity or wattage of the filament 21 and the heat exchange or heat loss capacity to the ambient environment across the body 711. The first is achieved by providing sufficient current rating in the filament while the second is a function of the surface area to effect the heat exchange.

Accordingly, body 711 may be convolved along its exterior to form a plurality of grooves 731 which may also aid the function of a grasping surface in the course of use. As before described, the shielding effect of the practitioner's palm over these heat exchange convolutions will tend to raise the effective steady state temperature of the compound during its application to the edges 112 of tray 111. In this manner manual skills can be acquired in the course of practicing the invention that will further enhance the comfort and quality of the denture produced.

Obviously, many modifications and variations can be effected without departing from the spirit of the invention instantly disclosed. It is therefore intended that the scope of the invention be determined solely by the claims appended hereto.

I claim:

1. Apparatus useful to a practitioner for depositing a ribbon of molten molding compound onto the peripheral edge of a denture impression tray, the compound being selected from a group of compounds that have a melting temperature that is greater than the normal temperature of a human and that is less than the temperature at which human tissue sustains injury, said compounds being available in the form of hardened cylindrical cartridges, comprising:

a dispenser body of an elongate form defined by a forward end and a rearward end including a central cavity extending generally between said forward and rearward ends, said central cavity having a sectional dimension substantially equal to the sectional dimension of said cartridges, said central cavity communicating to the exterior of said body at the rearward end for axial receipt of a sequence of said cartridges in the interior thereof;

a nozzle formed at said forward end of said body communicating with said central cavity;

an electrical heating element formed in said body adjacent said nozzle;

a temperature controller connected to said electrical heating element and conformed to sense the temperature of said central cavity adjacent said nozzle for controlling the electrical power applied to said element in accordance with the difference between the sensed temperature and a preselected temperature; and heat exchange means formed on said body proximate the rearward end thereof for transferring heat from said body to the ambient surrounding, said heat exchange means further providing manipulative surfaces for manual grasping by said practitioner, said heat exchange means includes laterally projecting hoops extending from said body and a handle surface projecting from said body rearwardly of said hoops.

2. Apparatus according to claim 1, further comprising:

manual adjustment means included in said temperature controller for accommodating manual adjustment of said preselected temperature.

3. Apparatus according to claim 2, wherein:

said manual adjustment means includes a potentiometer.

4. Apparatus according to claim 1, further comprising:

manual adjustment means included in said temperature controller for accommodating manual adjustment of said preselected temperature.

5. Apparatus according to claim 4, wherein:

said manual adjustment means includes a potentiometer.

6. A dispenser useful for a practitioner for depositing a bead of molten molding compound onto the peripheral edge of a denture impression tray, the compound being selected from a group of compounds that have a melting temperature that is greater than the normal temperature of a human and that is less than the temperature at which human tissue sustains injury, said compounds being available in the form of hardened cylindrical cartridges, comprising:

a dispenser body of an elongate form defined by a forward end and a rearward end and conformed for manual grasping by said practitioner proximate said rearward end including a central cavity extending generally between said forward and rearward ends, said central cavity having a sectional dimension substantially equal to the sectional dimension of said cartridges, said central cavity communicating to the exterior of said body at the rearward end for axial receipt of a sequence of said cartridges in the interior thereof, said body further including heat exchange surfaces formed proximate said rearward end thereof for transferring heat from said body to the ambient surrounding, said heat exchange surfaces further providing manipulative convenience in the course of manual grasping by said practitioner and said heat exchange surfaces including laterally projecting hoops extending from said body and a handle surface projecting from said body rearwardly of said hoops;

a nozzle formed at said forward end of said body communicating with said central cavity;

an electrical heating element formed in said body adjacent said nozzle; and a temperature controller connected to said electrical heating element and conformed to sense the temperature of said central cavity adjacent said nozzle for controlling the electrical power applied to said element in accordance with the difference between the sensed temperature and a preselected temperature.

7. Apparatus according to claim 6, further comprising:

manual adjustment means included in said temperature controller for accommodating manual adjustment of said preselected temperature.

8. Apparatus according to claim 7, wherein:

said manual adjustment means includes a potentiometer.

9. Apparatus according to claim 6, further comprising:

manual adjustment means included in said temperature controller for accommodating manual adjustment of said preselected temperature.

10. Apparatus according to claim 9, wherein:

said manual adjustment means includes a potentiometer.

11. A method for conforming a denture to the anatomical landmarks of a person, comprising the steps of:

forming a denture impression tray generally conformed to the maxillar or mandibular architectures of a patient;

reducing the dimension of the peripheral edge of said tray to provide a clearance for anatomical changes;

heating molding compound to melting in sufficient quantity to form a continuous bead on said peripheral edge;

maintaining said temperature in a range that is greater than normal body temperature of said patient and that is less than the temperature that causes tissue injury;

depositing a continuous bead of said heated molding compound onto said peripheral edge; and inserting said tray with said molding compound bead into said patient while said compound is still in its molten state.

12. A method according to claim 11, further comprising the step of:

selecting said molding compound from a group of compounds that has a melting temperature greater than said normal body temperature and less than said temperature that may cause tissue injury.

13. A method according to claim 12, comprising the further step of:

depositing impression compound onto said tray after said molding compound hardens and before the step of inserting said tray.

* * * * *

UNITED STATES PATENT AND TRADEMARK OFFICE
CERTIFICATE OF CORRECTION

PATENT NO.    : 6,524,102 B2                                            Page 1 of 1
DATED         : February 25, 2003
INVENTOR(S)   : Kerry N. Davis It is certified that error appears in the above-identified patent and that said Letters Patent is hereby corrected as shown below:

<u>Column 7,</u>
Line 32, change "for", first occurrence to -- to --

Signed and Sealed this

Fifteenth Day of July, 2003

JAMES E. ROGAN
*Director of the United States Patent and Trademark Office*